United States Patent [19]

Langsjoen et al.

[11] Patent Number: 5,011,858

[45] Date of Patent: Apr. 30, 1991

[54] THERAPY WITH COENZYME $Q_{10}$ OF PATIENTS HAVING AIDS OR OTHER RETROVIRAL DISEASES

[75] Inventors: Per H. Langsjoen, Temple; Karl A. Folkers, Austin; Peter H. Langsjoen, Bullard, all of Tex.

[73] Assignee: The Board of Regents, The University of Texas System, Austin, Tex.

[21] Appl. No.: 99,363

[22] Filed: Sep. 21, 1987

Related U.S. Application Data

[63] Continuation-in-part of Ser. No. 33,301, Mar. 30, 1987, abandoned.

[51] Int. Cl.$^5$ ............................................... A61K 31/12
[52] U.S. Cl. ..................................... 514/690; 424/94.1
[58] Field of Search ......................... 514/690; 424/94.1

[56] References Cited

U.S. PATENT DOCUMENTS 4,068,003 6/1986 Miyata .
4,156,718 7/1987 Bliznakov .
4,525,350 6/1985 Casey et al. ..................... 424/94.1

OTHER PUBLICATIONS

CA 103(17):135188h.
Dr. Emile G. Bliznakov and Gerald L. Hunt, The Miracle Nutrient Coenzyme $Q_{10}$, Bantam Books, New York, N.Y., 1986, pp. 1-7, 31-64, 203-209, and 220-232.
Bliznakov, et al., Experientia, 26:953-954 (1970).
Folkers, C&En, pp. 27-86, Apr. 21, 1986.
Yamaguchi, et al., J. Pharm. Pharmacol, 36:768-769 (1984).
Abstract 145017d, Pharmaceuticals, vol. 100 (1984).
Lucker, et al., Biomedical and Clinical Aspects of Coenzyme O, 4:143-151 (1984).
Sunamori, et al., Biomedical and Clinical Aspects of Coenzyme Q, 4:333-342 (1984).
Kanazawa and Takahashi, Biomedical and Clinical Aspects of Coenzyme Q, 3:31-42 (1981).
Kishi, et al., Biomedical and Clinical Aspects of Coenzyme Q, 3:67$\propto$78 (1981).
Entry No. 8113. Rifampin., The Merck Index, Tenth Edition, Martha Windholz (ed.) (1983).

Primary Examiner—Theodore Morris
Assistant Examiner—David M. Brunsman
Attorney, Agent, or Firm—Arnold, White & Durkee

[57] ABSTRACT

Therapy with a pharmaceutical formulation of coenzyme $Q_{10}$ ($CoQ_{10}$) of patients with Acquired Immune Deficiency Syndrome, known by the acronym AIDS and of patients with other retroviral diseases including the AIDS-related complex known as ARC is useful to reduce or negate opportunistic infections, adenopathy and other undesirable clinical symptoms. $CoQ_{10}$ therapy may be used in conjunction with antibiotic therapy to prevent or suppress secondary opportunistic infections.

16 Claims, No Drawings

THERAPY WITH COENZYME $Q_{10}$ OF PATIENTS HAVING AIDS OR OTHER RETROVIRAL DISEASES

This is a continuation-in-part application of U.S. patent application Ser. No. 033,301 filed Mar. 30, 1987 now abandoned.

BACKGROUND OF THE INVENTION

This invention relates to a new and safe therapy involving coenzyme $Q_{10}$ for human subjects who have retrovirus-related diseases such as Acquired Immune Deficiency Syndrome (AIDS) and the AIDS-Related Complex (ARC).

The direct or indirect causes of AIDS and other diseases including ARC, are now known to be certain retroviruses. The third human retrovirus to be identified is described as the human T-lymphotropic virus III (HTLV-III) and is also known as human immunodeficiency virus (HIV). A retrovirus is a virus having RNA as its primary genetic entity.

Mechanistically, $T_4$ helper-inducer lymphocytes appear to become infected with HIV. Normally, a single uninfected $T_4$ lymphocyte may proliferate to yield 1000 or more progeny. When a $T_4$ lymphocyte is infected with HIV, as few as 10 cells may result from such a proliferation. Infection with this virus results in a profound depletion of the $T_4$ lymphocyte population.

Patients with AIDS may develop a variety of threatening or lethal ancillary conditions such as pneumonia or Kaposi's sarcoma. This sarcoma is a tumor of blood vessel tissue in the skin or internal organs. The advent of AIDS and ARC has been viewed as a—"modern plague"—which has already killed an astounding number of people. Consequently, prophylactic treatment of uninfected individuals and therapy of patients afflicted with these retrovirus diseases have the highest priority.

Vaccination is one approach to therapy, but the task of producing an effective vaccine is particularly difficult because AIDS-related viruses have great genetic variability. This variability is the basis of a continuum of related retrovirus strains. An effective vaccine for widespread clinical use is not expected to soon be available.

Presently, the drugs or synthetic medicinals most commonly being tested as a treatment for AIDS are inhibitors of the unique retroviral enzyme, reverse transcriptase. Some of these are chemical analogues of nucleosides that form the subunits of DNA. One such drug is azidothymidine (AZT). This drug is known to have some toxicity and may suppress proliferation of bone marrow cells. Such effects may limit the use of AZT for the long periods of time likely to be necessary to control retroviral diseases.

One approach to the therapy or control of human retroviral disease is to resuscitate the depleted immune system of the patient. This approach has the potential to be effective despite the genetic variability of the retrovirus and to have important advantages over vaccines and classical medicinals.

The human immune system is complex and incompletely understood. No therapeutic approach has heretofore been established to improve the immune system in a manner enabling the control of retroviral disease. There are at least two general approaches for stimulation of the immune system by biochemical mechanisms. One such approach would be to use immune stimulants which are foreign to the human body and which may be categorized as nonspecific adjuvant-type medicinals. A second approach would be to pursue activation of intrinsic mechanisms of the immune system by using substances normally present, for example, in human tissue. The latter approach has prospect of beneficially stimulating the immune system while minimizing or avoiding undesirable side effects.

A study of the biochemistry and the immunology of lymphocytes reveals a wide array of interaction. For example, $T_4$ helper-inducer lymphocytes help plasma cells secrete antibody, induce maturation of $T_8$ cytotoxic cells and suppress maturation of B cells. The $T_4$ helper-inducer lymphocytes, under different circumstances, may induce maturation of B cells and proliferation of memory clones and induce $T_8$ suppressor cells. The $T_8$ suppressor cells in turn suppress differentiation to $T_8$ cells via the participation of suppressor factor.

Bliznakov et al., administered $CoQ_{10}$ to mice with tumors which had been induced by dibenzpyrene. They observed a resultant reduction of the percentage of mice with tumors, a reduction in the tumor size of those mice that developed tumors, and an increase in the number of survivors (Experientia, 26:953-954 (1970)). Bliznakov et al. used a parasitic model consisting of mice infected with *Plasmodium berghei* (a malarial organism) and found that the administration of $CoQ_{10}$ potentiated the effectiveness of chloroquine, increased survivors, prolonged survival time, and reduced parasitemia in red blood cells. It was suggested by Bliznakov et al. that $CoQ_{10}$ interacted in mechanisms of the immune system, but the specific nature of such interactions was unknown (*Book of Abstracts, VI International Meeting of the Reticuloendothelial Society*, Freiburg, Germany, p. 14 (1970); Bliznakov, In: The Reticuloendothelial System and Immune Phenomena, edited by DiLuzio, N. R., Plenum Press, N.Y., 315-322 (1971)).

Coenzyme $Q_{10}$ ($CoQ_{10}$) has been used for a variety of nutritional or medical purposes. $CoQ_{10}$ (2,3-dimethoxy-5-methyl-6-decaprenyl benzoquinone) may be an important component of the mitochondrial metabolic system and be related to efficient function of the immune system. A method for controlling and/or reversing immunological senescence in animals by administering $CoQ_{10}$ is described in U.S. Pat. No. 4,156,718. Coenzyme $Q_{10}$ use for treatment of myasthenia was described in U.S. Pat. No. 4,068,003.

The present invention resulted, at least in part, from research described herein which was directed toward restoration of depleted immune systems of AIDS patients.

SUMMARY OF THE INVENTION

The present invention involves a method for treating symptoms resulting from retrovirus infections such as those causing acquired immune deficiency syndrome or AIDS-related complex. This method comprises administration to a person suffering from such an infection of an effective amount of coenzyme $Q_{10}$ and continuing the administration at least until the symptoms of the infection have been alleviated.

The effective amount of coenzyme $Q_{10}$ utilized in the practice of the present invention is preferably a daily dose of between about 25 mg and about 400 mg, more preferably about 200 mg. The administration of the coenzyme $Q_{10}$ is preferably oral but could be parental if desired. If parental dosage were used, the coenzyme $Q_{10}$ would preferably be contained in an emulsion. The method of the present invention involves alleviation of AIDS or ARC related symptoms such as fatigue, malaise, adenopathy and pneumonia, for example. The coenzyme $Q_{10}$, particularly when administered orally, is preferably dissolved in an encapsulated vegetable oil such as soybean oil.

The present invention also comprises a method for the treatment of an individual infected with a retrovirus such as HIV, for example. The treatment method of the present invention for alleviation of symptoms, as described above, should be continued at least until symptoms of retrovirus infection have been alleviated. This may have resulted in total or virtually total elimination of resident retrovirus from the host's system, possibly involving activation of immune defenses. A concomitant treatment with antibiotic agents suppressing viral, fungal or bacterial infections is preferred in appropriate circumstances, particularly with secondary opportunistic infections, for example.

DESCRIPTION OF THE PREFERRED EMBODIMENT

The present invention involves therapy with coenzyme $Q_{10}$ ($CoQ_{10}$) of patients with retroviral infections. This treatment preferably involves oral administration of the $CoQ_{10}$. Parental $CoQ_{10}$ administration, such as intravenous, may be used, particularly for emergency situations. More specifically, the present invention relates to the partial or complete control of the clinical symptoms of such retrovirally-induced diseases. These diseases may be highly lethal and presently are not effectively and safely treated. The lethal symptoms may include infections and/or tumors which can occur because infected patients have a depressed immune function. In the case of these retroviral diseases, secondary conditions such as "opportunistic" infections or malignant disease may be extraordinarily serious. Undesirable clinical symptoms of AIDS may include dementia, fever, fatigue, anorexia, malaise, diarrhea, and painful adenopathy. Effective therapy for partial or total control of these direct and indirect retroviral diseases is essential to save and prolong life.

The present invention describes patients with AIDS or ARC and their treatment by administration of oral capsules of $CoQ_{10}$ during clinical observation. Because of the complexity of the multiple lymphocyte cell types, a specific favorable interaction of coenzyme $Q_{10}$ with one or more of these multiple cell types was unpredictable. The present invention comprises methods used in an exploratory clinical trial conducted to aid specific patients and because of the ominous prospect of an AIDS plague induced by these retroviruses. A prophylactic protection of those identified as susceptible to retrovirus-induced disease should also result from the dietary $CoQ_{10}$ supplementation of the present invention.

Capsules of $CoQ_{10}$ were orally administered to three patients diagnosed as having AIDS and four patients diagnosed as having ARC. These patients had histories generally indicating susceptibility to HTLV-III infection. The results of the administration of $CoQ_{10}$ to these seven patients with AIDS and ARC were greater than surprising—the results were startlingly successful. The initial disease status of these seven patients and the results of the treatment, on a patient-by-patient basis are exemplified as follows:

EXAMPLE 1

Coenzyme $Q_{10}$ was obtained from Kanegafuchi Chemical Industry Co. Ltd. (3-4, 3-Clone; Nakanashima, Kita-Ku, Osaka 530, Japan). The coenzyme $Q_{10}$ was dissolved in soybean oil and encapsulated in soft gelatin capsules by R. P. Scherer, North America (P.O. Box 5600, Clearwater, Fla. 33518). Each capsule contained about 33 mg $CoQ_{10}$. The orally administered dosage of $CoQ_{10}$ was 200 mg per day for each patient.

EXAMPLE 2

Patient 0144 was diagnosed as having AIDS. This 35-year old white male with a past history of intravenous drug abuse had *Pneumocystis carinii* pneumonia and disseminated cryptococcal infection. His serological HTLV III test was positive; the $T_4:T_8$ lymphocyte ratio was 0.16. Alleviation of symptoms by $CoQ_{10}$ administration was noted early on with later relapse of the Cryptococcal infection after $CoQ_{10}$ was stopped by the patient.

EXAMPLE 3

Patient 0200 was diagnosed as having AIDS. This 26-year old white male with a history of intravenous drug abuse was noted to have *Pneumocystis carinii* pneumonia on May 30, 1986. His HTLV III test was positive by both Enzyme Immunoassay (EIA) and Western Blot assay. He was started on $CoQ_{10}$ on Nov. 19, 1986. At a two-month follow-up examination, this patient was asymptomatic. This patient stopped his $CoQ_{10}$ and subsequently died of Mycobacterium avium intracellular infection on Apr. 25, 1987.

EXAMPLE 4

Patient 0201 was diagnosed as having AIDS. This 23-year old homosexual white male was noted to have disseminated histoplasmosis and pulmonary candidiasis on Aug. 20, 1986. His HTLV III test was positive by EIA and Western Blot, and he was anergic to the skin test battery. His $T_4:T_8$ lymphocyte ratio was 0.34. $CoQ_{10}$ was started on Oct. 9, 1986. In the outpatient clinic after three months, he was clinically doing very well and was asymptomatic. Other medication was the antifungal antibiotic drug ketoconazole, 200 mg BID. This patient's $CoQ_{10}$ blood levels did not increase. He presently had a disseminated Mycobacterium avium intracellular infection after 10 months of $CoQ_{10}$.

EXAMPLE 5

Patient 0202 was diagnosed as having ARC. This 27-year old white male, with a history of intravenous drug abuse, was noted to have Mycobacterium tuberculosis involving the left upper lobe, oral candidiasis and adenopathy on Aug. 6, 1986. His HTLV III test was positive by EIA and his $T_4:T_8$ lymphocyte ratio was 0.5. In a skin test, there was reaction only to PPD. Administration of $CoQ_{10}$ was started on Oct. 9, 1986. After three-months, he was clinically doing very well, was asymptomatic and without adenopathy. The patient left after his 3rd month of $CoQ_{10}$ and was lost to follow up.

EXAMPLE 6

Patient 0204 was diagnosed as having ARC. This 24-year old homosexual white male was noted to have fatigue, adenopathy and anal condylomata on Oct. 13, 1986. His HTLV III test was positive by EIA and Western Blot. He had anergy to a skin test battery. His $T_4:T_8$ lymphocyte ratio was 0.9. Administration of $CoQ_{10}$ was started on Dec. 16, 1986. In the outpatient clinic after eight months, he was asymptomatic and physically active.

EXAMPLE 7

Patient 0188 was diagnosed as having ARC. This 37-year old white male with pyruvate kinase hemolytic anemia had had multiple blood transfusions. The patient was noted, on Mar. 31, 1986, to have fatigue, malaise, adenopathy and right lower lobe pneumonia of undetermined etiology. He was HTLV III positive by EIA and Western Blot and his $T_4:T_8$ lymphocyte ratio was 0.33. Administration of $CoQ_{10}$ was started Oct. 17, 1986. After nine and one/half months, the patient was ambulatory, physically active and had an unremarkable examination.

EXAMPLE 8

Patient 0199 was diagnosed as having ARC. This 23-year old bisexual white male was noted, on Apr. 16, 1986, to have fatigue, malaise and adenopathy. He was HTLV III positive by EIA and Western Blot, and was anergic to the skin test battery; his $T_4:T_8$ lymphocyte ratio was 0.25. Administration of $CoQ_{10}$ was initiated on Oct. 26, 1986. After ten months, the patient was ambulatory, physically active, and had a normal physical examination. He left the program after ten months to start AZT therapy in Dallas, Tex.

EXAMPLE 9

Seven of the above seven patients with AIDS or ARC showed initial positive clinical responses to $CoQ_{10}$. The results of these clinical trials may be summarized as follows.

Three patients with AIDS (0200, 0201 and 0144) had pneumocystis pneumonia, histoplasmosis with pulmonary candidiasis and disseminated cryptococcal infection, respectively, in addition to positive diagnostic criteria of AIDS. In four months, four months, and two months, respectively, two of these patients were asymptomatic and were clinically doing very well, and one (0200) was stable. Later follow-up found that patient 0200 expired after $CoQ_{10}$ was stopped and that both patient 0201 and patient 0144 had had serious opportunistic infections, as well as low $CoQ_{10}$ blood levels.

Patient 0202 with ARC had Mycobacterium tuberculosis, oral candidiasis and adenopathy. After three months of oral $CoQ_{10}$ administration, he was asymptomatic and with no adenopathy and was clinically doing very well. This patient was lost to follow up after three months of treatment.

Patient 0204 with ARC had fatigue, adenopathy and anal condylomata. After three months of $CoQ_{10}$ administration, he had no adenopathy and no fatigue. At eight month follow-up, he continued to be doing very well.

Patient 0188 with ARC had fatigue, malaise, adenopathy and a right lower lobe pneumonia. After four months of $CoQ_{10}$ administration, this patient had no adenopathy and was clinically well. At the nine and onehalf month visit he continued to be doing very well.

Patient 0199 with ARC had malaise and adenopathy and after five months of $CoQ_{10}$ administration, there was no adenopathy and he was clinically much improved. At the 10 month visit he continues to do very well.

These examples of treatment for periods of up to only ten months illustrate the extremely encouraging clinical response to $CoQ_{10}$ administration of patients with retrovirus disease. Hopefully, symptomatic clinical improvement will continue beyond the treatment periods used up to the present time.

Five of these seven patients are still under treatment and are representative and are not restrictive. At present, the inventors are not aware of any other therapy which can bring about an asymptomatic status of patients with AIDS or ARC in 1 to 5 months. This is particularly true for a therapeutic agent which has the total safety of $CoQ_{10}$. $CoQ_{10}$ has been clinically used for over a decade on an approved basis in Japan in the treatment of a few million cardiac patients. No significant recorded side effects have been noted at the Koseisho ("Japanese F&DA"). Under the IND (7013) of the F.D.A. in the United States for treatment with $CoQ_{10}$ of patients with cardiomyopathy, there has not been a single verified side effect of medical significance.

It is believed that the use of $CoQ_{10}$ as described herein may be independently effective but may also be effectively used in conjunction with anti-viral drugs such as the nucleoside analog azidothymidine (AZT). Additionally, individuals identified as being susceptible to a possible retrovirus infections such as that resulting in AIDS and/or ARC should be prophylactically protected by administration of $CoQ_{10}$ according to the method of the present invention.

The following hypothetical examples are included to illustrate combined therapy with $CoQ_{10}$ and antibiotic drugs.

EXAMPLE 10

GENERAL SECONDARY INFECTIONS

Besides having greatly depressed immune systems, patients with AIDS or ARC are not only infected with various strains of retroviruses, but they may also be afflicted with pneumonia from *Pneumocystis carinii*, disseminated cryptococcal infection, disseminated histoplasmosis, oral or pulmonary candidiasis, tuberculosis or other secondary infections.

It is medically straightforward to provide such patients with at least two generic treatments, one treatment to improve significantly the immune system and the other treatment to control the "opportunistic" infections, such as pneumonia, tuberculosis, candidiasis, etc.

The dosage of the combined $CoQ_{10}$ and various antibiotic drugs will differ as to the weight of the patient, the schedule of the dosages, and the duration of treatment. Ultimately, as the immune system improves and the opportunistic infections are brought under control by appropriate drug therapy, such drug therapy could be appropriately withdrawn and the patient maintained on $CoQ_{10}$ to retain or further improve the immune system.

EXAMPLE 11

COMBINED THERAPY WITH $CoQ_{10}$ AND AZIDOTHYMIDINE (AZT)

The daily dosage of $CoQ_{10}$ should be about 200 mg per day but may be more or less, depending upon the subject and judgment of the treating physician. The $CoQ_{10}$ treatment may last indefinitely. The dosage of AZT (Zidovudine) would be about two 100 mg capsules, orally, ever 4 hours, for 24 hours and then indefinitely, or until the retrovirus is under control.

EXAMPLE 12

COMBINED THERAPY WITH CoQ$_{10}$ AND THERAPY FOR PNEUMOCYSTIS CARINII PNEUMONIA

For treatment of an AIDS patient with *Pneumocystis carinii* pneumonia, the daily dosage of CoQ$_{10}$ may be 200 mg, for indefinite duration. For the pneumonia, intravenous TRIMETHOPRIM and oral sulfamethoxazole, 15–20 mg/kg, each 6–8 hours would be taken for 14 days.

EXAMPLE 13

COMBINED THERAPY WITH CoQ$_{10}$ AND DRUGS FOR CRYPTOCOCCUS INFECTIONS

For an AIDS patient with cryptococcus infection the daily dosage of CoQ$_{10}$ may be 200 mg. Intravenous administration of Amphotericin B at a dosage of 0.3 mg. per kg per day would be administered along with oral Flucytosine at a daily dosage of 150 mg per kg. This therapy for cryptococcus infection may be continued for 6 weeks or as required.

EXAMPLE 14

COMBINED THERAPY WITH CoQ$_{10}$ AND DRUGS FOR TUBERCULOSIS

For a typical AIDS patient with tuberculosis the daily dosage of CoQ$_{10}$ may be 200 mg. For the tuberculosis, Isoniazide at a oral and daily dosage of 300 mg may be administered along with Rifampin at a daily oral dosage of 600 mg, and also with streptomycin at a daily dosage of 1 gram intramuscularly, for two months.

EXAMPLE 15

CONCEPT OF MULTIPLE THERAPY

The treatment of patients with debilitating disease such as AIDS or ARC only with CoQ$_{10}$ to improve the immune system would generally be inadvisable when additional treatment next be more effective. It would be medically mandatory, for example, to provide a therapy for the opportunistic infections which may occur because of the depressed immune system. This therapy should be with specific therapeutic drugs for specific opportunistic infections.

Such opportunistic infections are expected top be controlled by the specific drugs and also to be controlled by the continually improving immune system, due to the therapy with CoQ$_{10}$. In many cases, the specific drugs would be withdrawn after the infections are under control, but the administration of CoQ$_{10}$ will likely be continued indefinitely until the patient had been clinically well for a long time and obviously not susceptible to reoccurrence of an opportunistic infection. * * * *

Changes may be made in the methods of the present invention without departing from the spirit and scope of the present invention as defined in the following claims.

What is claimed is:

1. A method for treating symptoms of acquired immune deficiency syndrome or AIDS-related complex, said method an amount of Coenzyme Q$_{10}$ effective to alleviate the symptoms.

2. The method of claim 1 wherein the effective amount of coenzyme Q$_{10}$ is between about 25 mg and about 400 mg.

3. The method of claim 1 wherein the effective amount of coenzyme Q$_{10}$ is about 200 mg.

4. The method of claim 1, 2 or 3 wherein the administration is daily.

5. The method of claim 4 wherein the administration is oral.

6. The method of claim 1 wherein the symptoms include at least one of dementia, fever, anorexia, fatigue, malaise, adenopathy and pneumonia.

7. The method of claim 1 wherein the coenzyme Q$_{10}$ is contained in an encapsulated vegetable oil solution.

8. A method for the treatment of an individual having a retrovirus infection, the method comprising administering to the individual an amount of a composition consisting essentially of coenzyme Q$_{10}$ in an amount effective to alleviate symptoms of the retrovirus infection.

9. The method of claim 8 wherein the symptoms include at least one of fatigue, malaise, adenopathy and pneumonia.

10. The method of claim 8 wherein the effective amount of the composition contains between about 25 mg and about 400 mg coenzyme Q$_{10}$.

11. The method of claim 8 wherein the effective amount of the composition contains about 200 mg coenzyme Q$_{10}$.

12. The method of claim 8 or 9 wherein the administration is daily.

13. The method of claim 8 wherein the administration is oral.

14. The method of claim 8 wherein the coenzyme Q$_{10}$ is contained in an encapsulated vegetable oil solution.

15. The method of claim 8 wherein the retrovirus is HIV.

16. The method of claim 8 wherein the administration is parental and the coenzyme Q$_{10}$ is contained in an emulsion.

* * * * *

UNITED STATES PATENT AND TRADEMARK OFFICE
CERTIFICATE OF CORRECTION

PATENT NO. : 5,011,858

DATED : 4/30/91

INVENTOR(S) : Langsjoen et al

Page 1 of 2

It is certified that error appears in the above-identified patent and that said Letters Patent is hereby corrected as shown below:

At column 1, line 6, delete "patent" and replace with --Patent--.

At column 2, line 18, underline 'via'.

At column 2, line 19, underline 'et al.'

At column 2, line 24, underline 'experientia, 26 et'.

At column 2, line 25, underline 'al'.

At column 2, line 67, delete "parental" and replace with --parenteral--.

At column 3, line 2, delete "ARC related" and replace with --ARC-related--.

At column 6, line 65, delete "$CoQ_{10}$ treatment" and replace with --$CoQ_{10}$-treatment--.

In claim 1, column 8, line 9, after 'said method' and before 'an amount' insert --comprising administration to a person suffering therefrom--.

UNITED STATES PATENT AND TRADEMARK OFFICE
CERTIFICATE OF CORRECTION

PATENT NO. : 5,011,858
DATED : 4/30/91
INVENTOR(S) : Langsjoen et al

It is certified that error appears in the above-identified patent and that said Letters Patent is hereby corrected as shown below:

In claim 16, column 8, line 51, delete "parental" and replace with --parenteral--.

Signed and Sealed this

Seventeenth Day of November, 1992

Attest:

DOUGLAS B. COMER

*Attesting Officer*        *Acting Commissioner of Patents and Trademarks*